United States Patent
Ebenbeck et al.

(10) Patent No.: US 7,312,350 B2
(45) Date of Patent: Dec. 25, 2007

(54) PROCESS FOR PREPARING ARYLALKYNES

(75) Inventors: Wolfgang Ebenbeck, Köln (DE); Florian Rampf, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 10/751,844

(22) Filed: Jan. 5, 2004

(65) Prior Publication Data

US 2004/0192952 A1 Sep. 30, 2004

(30) Foreign Application Priority Data

Jan. 7, 2003 (DE) ............................... 103 00 124

(51) Int. Cl.
*C07C 17/38* (2006.01)

(52) U.S. Cl. .................. 558/56; 570/128; 570/185; 570/237; 548/373.1; 548/376.1

(58) Field of Classification Search ............... 570/128, 570/185; 548/376.1
See application file for complete search history.

(56) References Cited

U.S. PATENT DOCUMENTS

| | | | | |
|---|---|---|---|---|
| 3,848,010 | A | 11/1974 | Intille | 260/668 R |
| 5,300,521 | A | 4/1994 | Eberle et al. | 514/406 |
| 5,541,213 | A | 7/1996 | Matsukura et al. | 514/400 |
| 5,606,073 | A | 2/1997 | Matsukura et al. | 548/341.5 |
| 5,703,269 | A * | 12/1997 | Herrmann et al. | 560/19 |
| 6,005,151 | A * | 12/1999 | Herrmann et al. | 585/438 |
| 6,019,986 | A | 2/2000 | Banks | 424/265.1 |
| 6,090,394 | A | 7/2000 | Banks | 424/265.1 |
| 6,214,852 | B1 | 4/2001 | Kim et al. | 514/362 |
| 6,255,333 | B1 | 7/2001 | Banks | 514/406 |
| 6,316,675 | B1 * | 11/2001 | Reetz et al. | 568/335 |
| 6,392,053 | B2 | 5/2002 | Chen et al. | 548/185 |
| 6,414,156 | B2 | 7/2002 | Chen et al. | 546/209 |
| 6,515,004 | B1 | 2/2003 | Misra et al. | 514/369 |
| 6,534,531 | B2 | 3/2003 | Kimball et al. | 514/369 |
| 6,613,911 | B2 | 9/2003 | Chen et al. | 548/185 |
| 6,639,074 | B2 | 10/2003 | Chen et al. | 546/63 |
| 2001/0004639 | A1 | 6/2001 | Chen et al. | 514/369 |
| 2001/0006976 | A1 | 7/2001 | Chen et al. | 514/369 |
| 2001/0019780 | A1 | 9/2001 | Obata et al. | 428/607 |
| 2002/0058810 | A1 | 5/2002 | Talley et al. | 544/238 |
| 2002/0061915 | A1 | 5/2002 | Kimball et al. | 514/369 |
| 2002/0072609 | A1 | 6/2002 | Chen et al. | 546/269.7 |
| 2002/0099217 | A1 | 7/2002 | Chen et al. | 546/209 |
| 2002/0156115 | A1 | 10/2002 | Oda et al. | 514/407 |
| 2002/0173662 | A1 | 11/2002 | Banks | 546/275.4 |
| 2003/0191171 | A1 | 10/2003 | Oda et al. | 514/406 |
| 2003/0216440 | A1 | 11/2003 | Chen et al. | 514/340 |
| 2004/0063767 | A1 | 4/2004 | Chen et al. | 514/369 |

FOREIGN PATENT DOCUMENTS

| | | |
|---|---|---|
| EP | 719758 | 7/1996 |
| EP | 1008601 | 6/2000 |
| EP | 1260270 | 11/2002 |
| JP | 2001-294541 | 10/2001 |
| WO | 93/01173 | 1/1993 |
| WO | 98/42644 | 10/1998 |
| WO | 02/10093 | 2/2002 |

OTHER PUBLICATIONS

Chem. Ber., 115, (month unavailable) 1982, p. 828-831, H. J. Bestmann et al, "Reaktionen mit Phosphinalkylenen, XL [1,2]", no translation.
Chem. Ber., 98 (month unavailable) 1965, p. 3554-3560, K. Bodendorf et al, "Über die Darstellung und Fragmentierung von β-Chlor-acroleinen", no translation.
J. Gen. Chem. USSR, Bd. 33, (month unavailable), 1963, p. 158-162, A. V. Dombrovskii et al, "Haloarylation of Unsaturated Compounds with Aromatic Diazo Compounds. XVII. Arylation of α-Chlorostryrene and the Preparation of Tolans" XP009030547.
J. Org. Chem., 62, (month unavailable), 1997 , p. 8957-8960, E. Negishi et al, "Direct Synthesis of Terminal Alkynes via Pd-Catalyzed Cross Coupling of Aryl and Alkenyl Halides with Ethynylmetals Containing Zn, Mg, and Sn. Critical Comparison of Countercations".
Dept. of Chem. And Biochem., vol. 3, No. 12, Apr. 1, 2001, p. 1869-1871, B. H. Lipshutz et al, "Efficient Scavenging of $Ph_3P$ and $Ph_3P=O$ with High0Loading Merrifield Resin".
Chem. Commun., (month unavailable) 2002, p. 278-279, D. T.-Y. Bong et al, "Synthesis of bent [4]phenylene (cyclobuta[1,2-a:3,4-b']bisbiphenylene) and structure of a bis(trimethylsilyl) derivative: the last [4]phenylene isomer".
Chem. Pharm. Bull. 31(5), (month unavailable) 1983, p. 1751-1753, Y. Suzuki et al, "Formylation Of Phenols with Electron-withdrawing Groups in Strong Acids. Synthesis of Substituted Salicylaldehydes".
Syn. Comm., 30(3), (month unavailable) 2000, p. 397-403, G. V. M. Sharma et al, "Synthesis Of 5-Fluoro Salicylic Acid".
J. Org. Chem., v. 62, p. 895, Negishi Supplemental, p. 1-24, E. Negishi et al, "Direct Synthesis of Terminal . . . ".
J. Org. Chem., v. 62, p. 895, Negishi Supplemental, p. 1-24, E. Negishi et al, "Direct Synthesis of Terminal . . . ", 1997.

* cited by examiner

*Primary Examiner*—Rosalynd Keys
(74) *Attorney, Agent, or Firm*—Michael A. Miller

(57) ABSTRACT

The invention relates to a process for preparing arylvinyl halides and sulphonates and arylalkynes by reacting haloaromatics or aryl sulphonates with vinyl halides or sulphonates in the presence of a palladium catalyst and a base and, if appropriate, subsequent elimination.

26 Claims, No Drawings

PROCESS FOR PREPARING ARYLALKYNES

BACKGROUND OF THE INVENTION

1. Field of the Invention

The invention relates to a process for preparing arylvinyl halides and sulphonates and arylalkynes by reacting haloaromatics or aryl sulphonates with vinyl halides or sulphonates in the presence of a palladium catalyst and a base and, if appropriate, subsequent elimination.

2. Brief Description of the Prior Art

Arylalkynes have great industrial importance as fine chemicals, starting materials for polymers and intermediates for active compounds (cf. EP-A 571 326 and EP-A 1 219 173).

While process of preparing arylalkylenes are known, they are disadvantaged by drastic conditions for the preparation, low yield and other shortcomings, as discussed below. Arylalkynes can be prepared, for example, from aryl aldehydes by reaction with triphenylphosphine and $C_1$ building blocks such as methylene chloride or tetrabromomethane in the presence of strong bases (Chem. Ber., 1982, 115, 828 ff.). They can also be prepared by the reaction of electron-rich aromatics under Friedel-Crafts conditions to form acetyl aromatics with subsequent halogenation and elimination of hydrogen halide (Chem. Ber. 1965, 98, 3554 ff.).

Disadvantages of these processes are the often drastic conditions and at best moderate yields.

Also known for the preparation of arylalkynes is the reaction of haloaromatics with trimethylsilylacetylene (Chem. Comm. 2002, 278), acetylene (JP-A 2001 294541), trialkyltinacetylene (Org. Lett. 2001, 3, 1869) or alkynyl Grignard compounds (J. Org. Chem., 1997, 62, 8957-8960) in the presence of palladium catalysts.

These processes are disadvantaged by, the restricted availability of the alkyne building blocks in industrially relevant quantities and/or the difficulty of handling them and/or the undesirably high content of heavy metals present.

Further, known is the preparation of arylalkynes from arylolefins by halogenation of the double bond and subsequent elimination. However, a disadvantage of this method is the need to carry out the preparation in at least three reaction steps.

There is therefore a need to develop a process which makes it possible to prepare arylalkynes or particularly suitable precursors thereof from haloaromatics or aryl sulphonates in an efficient way.

SUMMARY OF THE INVENTION

In accordance with the foregoing, the present invention encompasses a process for preparing arylvinyl halides or sulphonates and arylalkynes which is characterized in that in a step A)

Compounds of the formula (I), $$Ar-[X]_n \qquad (I),$$

where n is one or two and

Ar is a substituted or unsubstituted aromatic or substituted or unsubstituted polyaromatic radical and X is in each case, independently of n, chlorine, bromine, iodine, a sulphonate or a diazonium salt, are reacted in the presence of a palladium catalyst and in the presence of at least one base and optionally in the presence of a salt and optionally in the presence of solvents with compounds of the formula (II),

(II)

where

Y is fluorine, chlorine, bromine, iodine, ($C_1$-$C_{12}$-alkyl) sulphonyloxy or ($C_1$-$C_{12}$-haloalkyl)sulphonyloxy and $R^1$ is hydrogen, cyano, $C_1$-$C_{12}$-alkyl, $C_6$-$C_{15}$-arylalkyl, $C_5$-$C_{14}$-aryl, fluorine, chlorine, COO($C_5$-$C_{14}$-aryl), COO($C_1$-$C_{12}$-alkyl), CON($C_5$-$C_{14}$-aryl)$_2$, CON($C_1$-$C_{12}$-alkyl)$_2$, OCO($C_5$-$C_{14}$-aryl) or OCO($C_1$-$C_{12}$-alkyl), to form compounds of the formula (III),

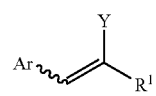
(III)

and optionally in a step B)

the compounds of the formula (III) are converted into compounds of the formula (IV)

(IV)

by reaction with base.

For the purposes of the invention, all definitions of radicals, parameters and explanations mentioned above or in the following, either generally or in preferred ranges, can be combined with one another in any way, i.e. also between the respective ranges and preferred ranges.

DETAILED DESCRIPTION OF THE INVENTION

For the purposes of the invention, alkyl and alkylene and alkoxy are each, independently of one another, a straight-chain, cyclic, branched or unbranched alkyl or alkylene or alkoxy radical which may be further substituted by $C_1$-$C_4$-alkoxy radicals. The same applies to the alkylene part of an arylalkyl radical.

For example, $C_1$-$C_4$-alkyl is methyl, ethyl, n-propyl, isopropyl, n-butyl or tert-butyl; $C_1$-$C_8$-alkyl can also be, for example, n-pentyl, cyclohexyl, n-hexyl, n-heptyl, n-octyl or isooctyl; $C_1$-$C_{12}$-alkyl can also be, for example, n-decyl or n-dodecyl and $C_1$-$C_{20}$-alkyl can also be n-hexadecyl or n-octadecyl.

For example, $C_1$-$C_4$-alkylene is methylene, 1,1-ethylene, 1,2-ethylene, 1,1-propylene, 1,2-propylene, 1,3-propylene, 1,1-butylene, 1,2-butylene, 2,3-butylene or 1,4-butylene; $C_1$-$C_8$-alkylene can also be 1,5-pentylene, 1,6-hexylene, 1,1-cyclohexylene, 1,4-cyclohexylene, 1,2-cyclohexylene or 1,8-octylene.

For example, $C_1$-$C_4$-alkoxy is methoxy, ethoxy, isopropoxy, n-propoxy, n-butoxy or tert-butoxy; $C_1$-$C_8$-alkoxy may also be cyclohexyloxy.

The general designation aryl as substituent encompasses carbocyclic radicals and heteroaromatic radicals in which no, one, two or three skeletal atoms per ring, but at least one skeletal atom in the total radical, is/are heteroatoms which are selected from the group consisting of nitrogen, sulphur and oxygen and may also bear one or more substituents which are selected independently from the group consisting of fluorine, nitro, cyano, di($C_1$-$C_8$-alkyl)amino, $C_1$-$C_8$-alkyl, $C_5$-$C_{14}$-aryl, $C_1$-$C_8$-fluoroalkyl, $C_1$-$C_8$-fluoroalkoxy, $C_1$-$C_8$-alkoxy, CO($C_1$-$C_8$-alkyl), COO-($C_1$-$C_8$)-alkyl and —CON($C_1$-$C_8$-alkyl)$_2$.

The same applies to the aryl part of an arylalkyl radical. $C_6$-$C_{15}$-arylalkyl may be by way of example and is preferably benzyl.

For the purposes of the invention, haloalkyl and fluoroalkyl are each, independently of one another, a straight-chain, cyclic, branched or unbranched alkyl radical which is substituted by one or more halogen atoms, or is fully substituted by halogen atoms, which are selected independently from the group consisting of fluorine, chlorine and bromine or are fluorine.

By way of example and preferably, $C_1$-$C_8$-haloalkyl is trifluoromethyl, trichloromethyl, 2,2,2-trifluoroethyl, pentafluoroethyl or nonafluorobutyl; $C_1$-$C_8$-fluoroalkyl is trifluoromethyl, 2,2,2-trifluoroethyl, pentafluoroethyl or nonafluorobutyl.

Protected formyl is a formyl radical which is protected by conversion into an aminal, acetal or a mixed aminal-acetal, with the aminals, acetals and mixed aminal-acetals being able to be acyclic or cyclic.

By way of example and preferably, protected formyl is a 1,1-(2,5-dioxy)cyclopentylene radical.

The preferred ranges for compounds of the formulae (I) to (IV) are defined as follows:

Ar is preferably a carbocyclic aromatic radical having from 6 to 24 skeletal carbon atoms, a carbocyclic bisaromatic or trisaromatic radical having from 6 to 10 carbon atoms per aromatic radical or a heteroaromatic radical having from 5 to 24 skeletal atoms in which no, one, two or three skeletal atoms per ring, but in the total molecule at least one skeletal atom, is/are heteroatoms selected from the group consisting of nitrogen, sulphur and oxygen. Furthermore, the carbocyclic aromatic radical, the carbocyclic bisaromatic or trisaromatic radical or the heteroaromatic radical may be substituted by up to 5 identical or different substituents per ring selected from the group consisting of hydroxy, chlorine, fluorine, nitro, cyano, free or protected formyl, $C_1$-$C_{12}$-alkyl, $C_5$-$C_{14}$-aryl, $C_6$-$C_{15}$-arylalkyl, —PO—[($C_1$-$C_8$)-alkyl]$_2$, —PO—[($C_5$-$C_{14}$)-aryl]$_2$, —PO—[($C_1$-$C_8$)-alkyl)($C_5$-$C_{14}$)-aryl)], tri($C_1$-$C_8$-alkyl)siloxyl and radicals of the formulae (Va-Vf), $$A-B-D-E \quad (Va)$$

$$A-E \quad (Vb)$$

$$A-SO_2-E \quad (Vc)$$

$$A-B-SO_2R^3 \quad (Vd)$$

$$A-SO_3W \quad (Ve)$$

$$A-COW \quad (Vf)$$

in which, independently of one another,
- A is absent or is a $C_1$-$C_8$-alkylene radical and
- B is absent or is oxygen, sulphur or $NR^2$,
  - where $R^2$ is hydrogen, $C_1$-$C_8$-alkyl, $C_6$-$C_{15}$-arylalkyl or $C_5$-$C_{14}$-aryl, and
- D is a carbonyl group and
- E is $R^3$, $OR^3$, $NHR^4$ or $N(R^4)_2$,
  - where $R^3$ is $C_1$-$C_8$-alkyl, $C_6$-$C_{15}$-arylalkyl, $C_1$-$C_8$-haloalkyl or $C_5$-$C_{14}$-aryl and
  - $R^4$ are each, independently of one another, $C_1$-$C_8$-alkyl, $C_6$-$C_{15}$-arylalkyl or $C_5$-$C_{14}$-aryl or $N(R^4)_2$ represents a cyclic amino radical and
- W is OH, $NH_2$, or OM where M can be an alkali metal ion, half an equivalent of an alkaline earth metal ion, an ammonium ion or an organic ammonium ion.

Ar is particularly preferably phenyl, naphthyl, phenanthrenyl, anthracenyl, biphenyl, binaphthyl, fluorenyl, pyridinyl, oxazolyl, thiophenyl, benzofuranyl, benzothiophenyl, dibenzofuranyl, dibenzothienyl, furanyl, indolyl, pyridazinyl, pyrazinyl, pyrimidinyl, triazolyl or quinolinyl, with the radicals mentioned being able to be further substituted by no, one, two or three radicals per ring which are selected independently from the group consisting of fluorine, nitro, cyano, di($C_1$-$C_4$-alkyl)amino, $C_1$-$C_4$-alkyl, $C_5$-$C_{10}$-aryl, $C_1$-$C_8$-fluoroalkyl, $C_1$-$C_8$-fluoroalkoxy, $C_1$-$C_8$-alkoxy, CO($C_1$-$C_4$-alkyl), COO—($C_1$-$C_4$)-alkyl, —CON($C_1$-$C_4$-alkyl)$_2$.

Ar is very particularly preferably a phenyl radical which may be further substituted by no, one, two or three radicals selected independently from the group consisting of fluorine, cyano, $C_1$-$C_4$-alkyl, $C_1$-$C_4$-alkoxy, trifluoromethyl, trifluoromethoxy, acetyl, COO—($C_1$-$C_4$)-alkyl and —CON($C_1$-$C_4$-alkyl)$_2$.

n is preferably 1.

X is preferably chlorine, bromine, iodine, trifluoromethanesulphonyloxy or nonafluorobutanesulphonyloxy, particularly preferably chlorine or bromine.

Very particularly preferred compounds of the formula (I) are:

p-trifluoromethylbromobenzene, o-trifluoromethylbromobenzene, m-trifluoromethylbromobenzene, 3,5-bis(trifluoromethyl)bromobenzene, o-cyanobromobenzene, p-bromobenzaldehyde and 4-bromo-1,5-dimethyl-3-(trifluoromethyl)-1H-pyrazole.

Y is preferably fluorine, chlorine, bromine, iodine, methanesulphonyloxy, p-toluenesulphonyloxy, trifluoromethanesulphonyloxy or nonafluorobutanesulphonyloxy, very particularly preferably fluorine, chlorine or bromine, more preferably chlorine.

$R^1$ is preferably hydrogen, cyano, $C_1$-$C_{12}$-alkyl, $C_5$-$C_{14}$-aryl, fluorine, chlorine, COO($C_5$-$C_{14}$-aryl), COO($C_1$-$C_{12}$-alkyl), OCO($C_5$-$C_{14}$-aryl) or OCO($C_1$-$C_{12}$-alkyl), particularly preferably hydrogen, cyano, fluorine or chlorine, very particularly preferably hydrogen.

Preferred compounds of the formula (II) are vinyl fluoride, vinyl chloride, vinyl bromide, 2-chloroacrylonitrile, methyl 2-chloroacrylate, butyl 2-chloroacrylate, 1,1-dichloroethylene, 1,1-difluoroethylene and 4-(1-chloroethenyl)-1,5-dimethyl-3-(trifluoromethyl)-1H-pyrazole, with vinyl chloride being particularly preferred.

In the process of the invention, step A) is carried out in the presence of a palladium catalyst.

As palladium catalyst, use is made of, by way of example and preferably, palladium complexes.

Palladium complexes can, for example, be generated in the reaction solution from palladium compounds and suitable ligands or can be used in the form of previously isolated palladium complexes.

Isolated palladium complexes which are suitable for the process of the invention are, for example, palladium complexes containing phosphorus compounds such as phosphines, phosphites, phosphonites or mixtures thereof, and preferably phosphines, as ligands.

As palladium complexes which can contain phosphorus compounds as ligands, use is made of, by way of example and preferably, complexes of the formula (VIa), $$[PdL_2An_2] \qquad (VIa)$$

where
- L are each a monophosphorus compound or
- $L_2$ together represents a diphosphorus compound and
- An is an anion, preferably chloride, bromide, iodide, acetate, propionate, allyl or cyclopentadienyl, or complexes of the formula (VIb), $$[PdL_m] \qquad (VIb)$$

where
- m is 2, 3 or 4 and
  where
- L can each be a monophosphorus compound or half an equivalent of a diphosphorus compound.

Monophosphorus compounds are, by way of example and preferably, compounds of the formula (VIIa), $$P(G-R^5)_3 \qquad (VIIa)$$

where
- G are each, independently of one another and independently of $R^5$, absent or oxygen and the radicals $R^5$ are each, independently of one another, $C_1$-$C_8$-alkyl or unsubstituted phenyl, naphthyl or ferrocenyl or phenyl, naphthyl or ferrocenyl substituted by one, two or three radicals $R^6$, where
  - $R^6$ is $C_1$-$C_8$-alkyl, $C_1$-$C_8$-alkoxy, chloro, fluoro, $N(C_1$-$C_6$-alkyl$)_2$, $CO_2$—($C_1$-$C_8$-alkyl), —CON($C_1$-$C_8$-alkyl$)_2$, cyano or CO($C_1$-$C_8$-alkyl).

Particularly preferred monophosphorus compounds are compounds of the formula (VIIa) in which G is absent and $R^5$ are each, independently of one another, $C_1$-$C_8$-alkyl or unsubstituted phenyl, naphthyl or ferrocenyl or phenyl, naphthyl or ferrocenyl substituted by one, two or three radicals $R^6$, where
- $R^6$ is $C_1$-$C_8$-alkyl, $C_1$-$C_8$-alkoxy, chlorine or fluorine.

Very particularly preferred monophosphorus compounds are compounds of the formula (VIIa) in which G is absent, and two or three of the radicals $R^5$ are each, independently of one another, $C_1$-$C_8$-alkyl and no or one radical $R^5$ is unsubstituted phenyl or naphthyl or phenyl or naphthyl substituted by one, two or three radicals $R^6$, where
- $R^6$ is $C_1$-$C_8$-alkyl, $C_1$-$C_8$-alkoxy, chlorine or fluorine.

Even more preferred monophosphorus compounds are triphenylphosphine, tri(tert-butyl)phosphine, phenyldi(tert-butyl)phosphine and ferrocenyldi(tert-butyl)-phosphine.

Diphosphorus compounds are, by way of example and preferably, compounds of the formula (VIIb), $$(R^7-G)_2P-G-Z-G-P(G-R^7)_2 \qquad (VIIb)$$

where
- G are each, independently of one another and independently of $R^7$ and Z, absent or oxygen and
- the radicals $R^7$ are each, independently of one another, $C_1$-$C_8$-alkyl or unsubstituted phenyl, naphthyl or heteroaryl having from 5 to 12 skeletal carbon atoms or phenyl, naphthyl or heteroaryl having from 5 to 12 skeletal carbon atoms substituted by one, two or three radicals $R^8$, where
  - $R^8$ are each selected independently from the group consisting of $C_1$-$C_8$-alkyl, $C_1$-$C_8$-alkoxy, fluorine and cyano, and
- Z is an unsubstituted or substituted radical selected from the group consisting of $C_1$-$C_4$-alkylene, 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl.

Preferred diphosphorus compounds are 1,3-bis(diisopropylphosphino)propane, 1,4-bis(diisopropylphosphino)butane, 2,2'-bis(diphenylphosphino)-1,1'-binaphthyl.

Preference is given to using complexes which contain monophosphorus compounds as ligands.

Preferred isolated palladium complexes are bis(tri-t-butylphosphine)palladium(II) dichloride, bis(di-tert-butylphenylphosphine)palladium(II) dichloride, bis(di-tert-butylferrocenylphosphine)palladium(II) dichloride, (tricyclohexylphosphine)(diallyl ether)palladium(0) complex, bis(tricyclohexylphosphine)palladium(0).

In the process of the invention, palladium complexes which are generated in the reaction solution from palladium compounds and ligands are preferred as palladium catalysts.

As palladium compounds it is possible to use, by way of example and preferably, $Pd_2$(dibenzylideneacetone)$_3$ or allylpalladium chloride or bromide or compounds of the formula (VIIIa), $$Pd(Y^1)_2 \qquad (VIIIa)$$

where
- $Y^1$ is an anion, preferably chloride, bromide, acetate, propionate, nitrate, methane sulphonate, trifluoromethanesulphonate, acetylacetonate, allyl or cyclopentadienyl, or palladium compounds of the formula (VIIIb), $$Pd(Y^2)_2L_2 \qquad (VIIIb)$$

where
- $Y^2$ is an anion, preferably chloride, bromide, acetate, methanesulphonate, nonafluorobutanesulphonate or trifluoromethanesulphonate, tetrafluoroborate or hexafluorophosphate and
- L are each a nitrile, preferably acetonitrile, benzonitrile or benzyl cyanide, or an olefin, and preferably cyclohexene or cyclooctene, or
- $L_2$ together represents a diolefin, preferably norbornadiene or 1,5-cyclooctadiene, or palladium compounds of the formula (VIIIc), $$M_2[Pd(Y^3)_4] \qquad (VIIIc)$$

where
- $Y^3$ is a halide, preferably chloride or bromide, and
- M is lithium, sodium, potassium, ammonium or organic ammonium.

Preferred palladium compounds are palladium(II) acetate, palladium(II) chloride, palladium(II) bromide, palladium(II) propionate, palladium(II) acetylacetonate, lithium, sodium or potassium tetrachloropalladate, bis(benzonitrile)palladium(II) chloride, bis(acetonitrile) palladium(II) chloride.

As ligands for generating palladium complexes in the reaction solution, preference is given to using phosphorus compounds of the formulae (VIIa) and (VIIb), with monophosphorus compounds of the formula (VIIa) being more preferred. The abovementioned preferred ranges apply in the same way.

The molar ratio of phosphorus to palladium in the reaction mixture can be, for example, from 1:1 to 10:1, preferably from 2:1 to 5:1, and particularly preferably from 3:1 to 4:1.

In step A) according to the invention, the molar ratio of X to be replaced in compounds of the formula (I) to palladium can be, for example, from 10 to 20,000, preferably from 50 to 5000, and very particularly preferably from 100 to 2000.

The process of the invention is carried out in the presence of at least one, and preferably one, base.

Suitable bases are, for example, ionic bases, amines or N-heteroaromatic compounds.

Preferred amines are, by way of example and preferably, amines of the formula (IX), $$NR^9R^{10}R^{11} \quad (IX)$$

where $R^9$, $R^{10}$ and $R^{11}$ are each, independently of one another, $C_1$-$C_{12}$-alkyl, $C_5$-$C_{14}$-aryl or $C_6$-$C_{15}$-arylalkyl, or two or three of the radicals $R^9$, $R^{10}$ and $R^{11}$ together with the nitrogen atom can form a monocyclic, bicyclic or tricyclic heterocycle having from 4 to 8 carbon atoms per ring.

Ionic bases for the purposes of the invention are, for example, alkali metal carboxylates and alkaline earth metal carboxylates such as acetates, propionates, benzoates, alkali metal and alkaline earth metal alkoxides, amides, hydrides, alkali metal and alkaline earth metal carbonates, hydrogen carbonates, phosphates, hydrogen phosphates, hydroxides. Alkali metals are preferably lithium, sodium, potassium and caesium; alkaline earth metals are preferably calcium, magnesium and barium.

Preferred N-heteroaromatic compounds are, for example, pyridines such as pyridine, 2,6-dimethylpyridine, 2-, 3- or 4-N,N-dimethylaminopyridine or 2-, 3- or 4-picoline and also quinolines such as quinoline or 2-methylquinoline.

The process of the invention is particularly preferably carried out using bulky nitrogen bases such as ethyldiisopropylamine, triisopropylamine, diisopropylaniline, triisobutylamine, ethyldiisobutylamine, dicyclohexylmethylamine, dicyclohexylethylamine, cyclohexyldiethylamine, cyclohexyldimethylamine and 2,6-bis(diisopropyl)pyridine, with preference being given to dicyclohexylmethylamine, dicyclohexylethylamine and cyclohexyldimethylamine.

The amount of base used can be, for example, from 0.8 to 200 times, preferably from 1 to 3 times and more preferably from 1.0 to 1.2 times, the molar amount of X to be replaced in compounds of the formula (I).

The process of the invention may be carried out in the presence of a salt. Suitable salts for the process of the invention are, by way of example and preferably, salts of the formula (X), $$(Cation^+)(Anion^-) \quad (X)$$

where (Cation$^+$) is a substituted ammonium, phosphonium or arsonium cation or an alkali metal ion and
(Anion$^-$) is the anion of an organic or inorganic acid.
(Cation$^+$) is preferably a cation of the formula (XI), $$[Pnyc(C_1\text{-}C_{12}\text{-alkyl})_p(C_6\text{-}C_{15}\text{-arylalkyl})_q(C_5\text{-}C_{14}\text{-aryl})_r]^+ \quad (XI)$$

where

Pnyc is nitrogen, phosphorus or arsenic, preferably nitrogen, and (p+q+r)=4.

(Cation$^+$) is particularly preferably tetrabutylammonium, tetraphenylammonium, tetraphenylphosphonium, tetrabutylphosphonium.

(Anion$^-$) is preferably fluoride, chloride, bromide, iodide, cyanate, thiocyanate, acetate, hydroxide, nitrate, hydrogen sulphate, tetrafluoroborate, hexafluorophosphate, tosylate or triflate, particularly preferably chloride, bromide, iodide.

Very particularly preferred salts are tetrabutylammonium chloride, tetrabutylammonium bromide, tetraphenylammonium bromide, tetrabutylphosphonium chloride, tetrabutylphosphonium bromide, tetraphenylphosphonium chloride and tetraphenylphosphonium bromide or mixtures thereof. Further preference is given to tetrabutylammonium bromide.

The salts can, for example, be used in amounts of from 0.01 to 100 mol % based on the compound which limits the theoretical yield (compound of the formula (I) or compound of the formula (II)), preferably in amounts of from 0.1 to 15 mol %, particularly preferably in amounts of from 0.5 to 5 mol %. The use of larger amounts and also salt melts are possible.

The amount of compound of the formula (II) used can be, for example, from 0.2 to 200 times (when used as solvent) the molar amount of X to be replaced in the compound of the formula (I), and is preferably from 0.5 to 30 times, particularly preferably from 0.8 to 5 times, this molar amount.

If compounds of the formula (I) bearing free acid groups such as sulphonic acid or carboxylic acid groups are used, the amount of the base used has to be increased correspondingly.

Step A) may be carried out in the presence of solvents, preferably in the presence of an aprotic solvent, particularly preferably in the presence of a polar aprotic solvent. In the present context, aprotic means that the solvent contains no protons which, based on an aqueous comparison scale at 25° C., have a p$K_a$ of less than 20. Polar means that the solvent has a dielectric constant ∈ at 25° C. of at least 4.

Preferred aprotic solvents are: ethers such as dioxane, THF, 1,2-dimethoxyethane, diethylene glycol dimethyl ether, tetraethylene glycol dimethyl ether; amide solvents such as dimethylformamide, N-methylpyrrolidone, N-methylcaprolactam or dimethylacetamide; nitriles such as acetonitrile, benzonitrile and benzyl cyanide; ketones such as dimethyl ketone, diethyl ketone and methyl tert-butyl ketone; sulphoxides such as dimethyl sulphoxide and sulphones such as tetramethylene sulphone, or mixtures of such solvents.

The amount of any solvent used can be, for example, from 50 ml to 5000 ml, preferably from 100 to 500 ml, per mol of the compound of the formula (I).

The reaction temperature in step A) can be, for example, from 20° C. to 200° C., preferably from 80 to 150° C. and particularly preferably from 100° C. to 140° C.

The reaction of step A) can be carried out at, for example, from 0.2 to 100 bar; preference is given to ambient pressure or the pressure which is established in a closed vessel at the reaction temperature.

The reaction time in step A) can be, for example, from 0.2 hour to 72 hours; preference is given to from 1 to 20 hours.

The reaction is preferably carried out under a protective gas atmosphere with substantial exclusion of oxygen and moisture. Suitable protective gases are, for example, nitrogen and noble gases such as argon or mixtures of such gases.

In a preferred embodiment of step A) according to the invention, the compound of the formula (I) together with the compound of the formula (II), the base, if desired the salt, the ligand and the palladium compound are placed in a pressure-rated reaction vessel under protective gas and the mixture is heated to the reaction temperature while stirring. After the reaction is complete, the mixture is poured into water. Solid products precipitate and can be filtered off with suction and, for example, washed with water. Liquid products can be extracted by means of an organic solvent which is immiscible or sparingly miscible with water and, for example, worked up by distillation.

If a gaseous compound of the formula (II) is used, this is preferably added to the mixture as last reaction component and its excess is removed after the end of the reaction by careful depressurization. The reaction mixture is then worked up further as described.

Solid products can, if desired, be purified further by, for example, recrystallization or reprecipitation.

It can be advantageous to carry out the reaction under addition control by metering in the compound of the formula (II) at the reaction temperature during the reaction.

It may also be advantageous to add free-radical inhibitors such as 2,6-di-tert-butylphenol in step A) in order to suppress secondary free-radical reactions.

As an alternative, the palladium catalyst can be added only during the course of the reaction or can be generated during the reaction by addition of ligand or palladium compound. The simultaneous introduction of compounds of the formula (II) and palladium catalyst or ligand or palladium compound is also possible.

It is advantageous to use a weakly acidic aqueous solution in the work-up to bind any remaining base as salt. The base can, for example, be recovered by alkalization and extraction of the washing liquid with an organic solvent.

If desired, the compounds of the formula (III) can be converted by elimination into compounds of the formula (IV) in a step B).

The elimination is preferably carried out in the presence of base in an organic solvent. Examples of bases which can be used are:

Alkali metal or alkaline earth metal hydrides, hydroxides, amides, alkoxides, for example sodium hydride, sodium amide, lithium diethylamide, sodium methoxide, sodium ethoxide, potassium tert-butoxide, sodium hydroxide, potassium hydroxide, tertiary amines such as trimethylamine, triethylamine, tributylamine, diisopropylethylamine, piperidine, N-methylpiperidine, N,N-dimethylaminopyridine, diazabicyclooctane (DABCO), diazabicyclononene (DBN) or diazabicycloundecene (DBU) and also N-heteroaromatic compounds such as pyridine and 3-N,N-dimethylaminopyridine.

In the case of compounds of the formula (III) in which Y is chlorine, preference is given, depending on the substitution pattern, to organolithium compounds such as methyllithium or n-butyllithium or alkali metal or alkaline earth metal hydrides, amides or alkoxides. Bases which have been found to be particularly useful here are, for example, potassium tert-butoxide, sodium or sodium amide in ammonia or various ethers and also methyllithium or n-butyllithium in THF or diethyl ether.

In the case of compounds of the formula (III) in which Y is bromine, preferred bases are, apart from the bases and base/solvent combinations mentioned for the analogous chlorine compounds, hydroxides in polar solvents.

The elimination can be carried out at, for example, temperatures of from −20 to 200° C., preferably from 20 to 180° C., particularly preferably from 80 to 180° C.

The reaction time in step B) can be, for example, from 0.5 to 72 hours, preferably from 2 to 24 hours.

The pressure in step B) is not critical and can be, for example, from 0.5 to 100 bar, preferably from 0.8 to 3 bar. Particular preference is given to ambient pressure.

The work-up in step B) can be carried out in a known manner, for example by extraction and subsequent removal of volatile constituents.

In one embodiment of the process of the invention, step B) can, for example, be carried out by addition of base to the reaction mixture obtained in step A) without intermediate isolation of compounds of the formula (III).

The process of the invention is particularly useful for preparing 4-ethynyl-1,5-dimethyl-3-(trifluoromethyl)-1H-pyrazole, 4-(2-chloroethenyl)-1,5-dimethyl-3-(trifluoromethyl)-1H-pyrazole, 4-(2-bromoethenyl)-1,5-dimethyl-3-(trifluoromethyl)-1H-pyrazole, 4-(2-methoxycarbonylethenyl)-1,5-dimethyl-3-(trifluoromethyl)-1H-pyrazole and 4-(2-ethoxycarbonylethenyl)-1,5-dimethyl-3-(trifluoromethyl)-1H-pyrazole, which are likewise encompassed as substances by the invention.

The compounds of the formulae (III) and (IV) which can be prepared according to the invention are suitable, in particular, for use in a process for preparing pharmaceuticals or agrochemicals.

The compounds of the formulae (III) and (IV) which can be prepared according to the invention and the last-named individual compounds of the formula (IV) are particularly useful for the preparation of acaricides.

An advantage of the invention is that arylvinyl halides and sulphonates and arylalkynes can be obtained in high yields in a simple and efficient manner according to the invention.

EXAMPLES

Example 1

Preparation of 4-(2-chloroethenyl)-1,5-dimethyl-3-(trifluoromethyl)-1H-pyrazole 2.0 g of 4-bromo-1,5-dimethyl-3-(trifluoromethyl)-1H-pyrazole together with 18.5 mg of palladium acetate, 73.2 mg of di(tert-butyl)phenylphosphine, 60.3 mg of tetrabutylammonium bromide, 10 mg of hydroquinone, 1.8 g of dicyclohexylmethylamine and 23 ml of dimethylacetamide are placed in a stainless steel autoclave. 2.6 g of vinyl chloride are condensed into this autoclave at low temperature and the autoclave is subsequently closed. It is subsequently heated at 140° C. for 20 hours. It is then cooled and depressurized and the reaction mixture is dewatered and worked up by extraction. 1.53 g (83% of theory) of 4-(2-chloroethenyl)-1,5-dimethyl-3-(trifluoromethyl)-1H-pyrazole are isolated.

Example 2

Preparation of 4-ethynyl-1,5-dimethyl-3-(trifluoromethyl)-1H-pyrazole 1.27 g (5.67 mmol) of 4-(2-chloroethenyl)-1,5-dimethyl-3-(trifluoromethyl)-1H-pyrazole from Example 1 are dissolved in 40 ml of dry THF and placed under a protective gas atmosphere. After cooling the reaction solution to 0° C., 1.91 (17.0 mmol) of potassium tert-butoxide are introduced and, after the addition is complete, the mixture is stirred at 20° C. for 3 hours. After the end of the reaction, a saturated ammonium chloride solution (25 ml) is added and the mixture is extracted twice with 30 ml each time of methylene chloride. The combined organic phases are dried over magnesium sulphate, the solvent is removed by distillation and 4-ethynyl-1,5-dimethyl-3-(trifluoromethyl)-1H-pyrazole is isolated as a microcrystalline solid in a yield of 79% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for arylalkynes, comprising:
in a step A)
reacting compounds of the formula (I),

  (I), where
n is one or two and
Ar is a substituted or unsubstituted aromatic or substituted or unsubstituted polyaromatic radical and
X is, in each case independently, chlorine, bromine, iodine, a sulphonate or a diazonium salt,
in the presence of a palladium catalyst and
in the presence of at least one base;
with compounds of the formula (II),

  (II)

where
Y is fluorine, chlorine, bromine, iodine, ($C_1$-$C_{12}$-alkyl)sulphonyloxy or ($C_1$-$C_{12}$-haloalkyl)sulphonyloxy and
$R^1$ is hydrogen, cyano, $C_1$-$C_{12}$-alkyl, $C_5$-$C_{14}$-aryl, fluorine, chlorine, COO($C_5$-$C_{14}$-aryl), COO($C_1$-$C_{12}$-alkyl), CON($C_5$-$C_{14}$-aryl)$_2$, CON($C_1$-$C_{12}$-alkyl)$_2$, OCO($C_5$-$C_{14}$-aryl) or OCO($C_1$-$C_{12}$-alkyl),
to form compounds of the formula (III),

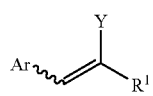  (III)

and in a step B)
reacting the compounds of the formula (III) with a base to convert it into compounds of the formula (IV).

  (IV).

2. Process according to claim 1, characterized in that step A) is carried out in the presence of a salt.

3. Process according to claim 1, characterized in that step A) is carried out in the presence of solvents.

4. Process according to claim 1, characterized in that Ar is a carbocyclic aromatic radical having from 6 to 24 skeletal carbon atoms, a carbocyclic bisaromatic or trisaromatic radical having from 6 to 10 carbon atoms per aromatic radical or a heteroaromatic radical having from 5 to 24 skeletal atoms in which no, one, two or three skeletal atoms per ring, but at least one skeletal atom in the total molecule, is/are heteroatoms selected from the group consisting of nitrogen, sulphur and oxygen, where the carbocyclic aromatic radical, the carbocyclic bisaromatic or trisaromatic radical or the heteroaromatic radical is optionally substituted by up to 5 identical or different substituents per ring which are selected from the group consisting of hydroxy, chlorine, fluorine, nitro, cyano, free or protected formyl, $C_1$-$C_{12}$-alkyl, $C_5$-$C_{14}$-aryl, $C_6$-$C_{15}$-arylalkyl, —PO—[($C_1$-$C_8$)-alkyl]$_2$, —PO—[($C_5$-$C_{14}$)-aryl]$_2$, —PO—[($C_1$-$C_8$)-alkyl)($C_5$-$C_{14}$)-aryl)], tri($C_1$-$C_8$-alkyl)siloxyl and radicals of the formulae (Va-f),

| A—B—D—E | (Va) |
| A—E | (Vb) |
| A—SO$_2$—E | (Vc) |
| A—B—SO$_2$R$^3$ | (Vd) |
| A—SO$_3$W | (Ve) |
| A—COW | (Vf) | in which, independently of one another,
A is absent or is a $C_1$-$C_8$-alkylene radical and
B is absent or is oxygen, sulphur or NR$^2$,
where R$^2$ is hydrogen, $C_1$-$C_8$-alkyl, $C_6$-$C_{15}$-arylalkyl or $C_5$-$C_{14}$-aryl, and
D is a carbonyl group and
E is R$^3$, OR$^3$, NHR$^4$ or N(R$^4$)$_2$,
where R$^3$ is $C_1$-$C_8$-alkyl, $C_6$-$C_{15}$-arylalkyl, $C_1$-$C_8$-haloalkyl or $C_5$-$C_{14}$-aryl and
R$^4$ are each, independently of one another, $C_1$-$C_8$-alkyl, $C_6$-$C_{15}$-arylalkyl or $C_5$-$C_{14}$-aryl, or N(R$^4$)$_2$ represents a cyclic amino radical and
W is OH, NH$_2$, or OM where M can be an alkali metal ion, half an equivalent of an alkaline earth metal ion, an ammonium ion or an organic ammonium ion.

5. Process according to at claim 1, characterized in that X is chlorine, bromine, iodine, trifluoromethanesulphonyloxy or nonafluorobutanesulphonyloxy.

6. Process according to claim 1, characterized in that Y is fluorine, chlorine, bromine, iodine, methanesulphonyloxy, p-toluenesulphonyloxy, trifluoromethanesulphonyloxy or nonafluorobutanesulphonyloxy.

7. Process according to claim 1, characterized in that R$^1$ is hydrogen, cyano, $C_1$-$C_{12}$-alkyl, $C_5$-$C_{14}$-aryl, fluorine, chlorine, COO($C_5$-$C_{14}$-aryl), COO($C_1$-$C_{12}$-alkyl), OCO($C_5$-$C_{14}$-aryl) or OCO($C_1$-$C_{12}$-alkyl).

8. Process according to claim 1, characterized in that compounds of the formula (II) used are vinyl fluoride, vinyl chloride, vinyl bromide, 2-chloroacrylonitrile, methyl 2-chloroacrylate, butyl 2-chloroacrylate, 1,1-dichloroethylene, 1,1-difluoroethylene or 4-(1-chloroethenyl)-1,5-dimethyl-3-(trifluoromethyl)-1H-pyrazole.

9. Process according to claim 1, characterized in that palladium complexes generated in the reaction solution from suitable ligands or palladium complexes which have previously been isolated are used as palladium catalyst.

10. Process according to claim 1, characterized in that bases used are ionic bases, amines or N-heteroaromatic compounds.

11. Process according to claim 1, characterized in that free-radical inhibitors are added in step A).

12. Process according to claim 1, characterized in that bases used are alkaline earth metal or alkali metal hydrides, hydroxides, amides, alkoxides, tertiary amines and/or N-heteroaromatic compounds.

13. Process according to claim 1, characterized in that 4-ethynyl-1,5-dimethyl-3-(trifluoromethyl)-1H-pyrazole, is prepared.

14. Process according to claim 1, wherein the palladium catalyst is selected from palladium catalyst of formula (VIa):

$$[PdL_2An_2] \quad (VIa)$$

wherein

L are each a monophosphorous compound; or $L_2$ together are a diphosphorous compound; and An is an anion selected from chloride, bromide, acetate, propionate, allyl, and/or cyclopentadiene;

and formula (VIb):

$$[PdL_m] \quad (VIb)$$

wherein

L is a monophosphorous or half equivalent of a diphosphorous compound; and m is 2, 3, or 4.

15. Process according to claim 14, characterized in that step A) is carried out In the presence of a salt.

16. Process according to claim 14, characterized in that step A) is carried out in the presence of solvents.

17. Process according to claim 14, characterized in that Ar is a carbocyclic aromatic radical having from 6 to 24 skeletal carbon atoms, a carbocyclic bisaromatic or trisaromatic radical having from 6 to 10 carbon atoms per aromatic radical or a heteroaromatic radical having from 5 to 24 skeletal atoms in which no, one, two or three skeletal atoms per ring, but at least one skeletal atom in the total molecule, is/are heteroatoms selected from the group consisting of nitrogen, sulphur and oxygen, where the carbocyclic aromatic radical, the carbocyclic bisaromatic or trisaromatic radical or the heteroaromatic radical is optionally substituted by up to 5 identical or different substituents per ring which are selected from the group consisting of hydroxy, chlorine, fluorine, nitro, cyano, free or protected formyl, $C_1$-$C_{12}$-alkyl, $C_5$-$C_{14}$-aryl, $C_6$-$C_{15}$-arylalkyl, -PO-[($C_1$-$C_8$)-alkyl]$_2$, -PO-[($C_5$-$C_{14}$)-aryl]$_2$, -PO-[($C_1$-$C_8$)-alkyl)($C_5$-$C_{14}$)-aryl)], tri($C_1$-$C_8$-alkyl)siloxyl and radicals of the formulae (Va-f), A-B-D-E (Va)

A-E (Vb)

A-SO$_2$-E (Vc)

A-B-SO$_2$R$^3$ (Vd)

A-SO$_3$W (Ve)

A-COW (Vf)

in which, independently of one another,

A is absent or is a $C_1$-$C_8$-alkylene radical and

B is absent or is oxygen, sulphur or NR$^2$, where R$^2$ is hydrogen, $C_1$-$C_8$-alkyl, $C_6$-$C_{15}$-arylalkyl or $C_5$-C14-aryl, and D is a carbonyl group and E is R$^3$, OR$^3$, NHR$^4$ or N(R$^4$)$_2$, where R$^3$ is $C_1$-$C_8$-alkyl, $C_6C_{15}$-arylalkyl, $C_1$-$C_8$-haloalkyl or $C_5$-$C_{14}$-aryl and R$^4$ are each, independently of one another, $C_1$-$C_8$-alkyl, $C_6$-$C_{15}$-arylalkyl or $C_5$-$C_{14}$-aryl, or N(R$^4$)$_2$ represents a cyclic amino radical and W is OH, NH$_2$, or OM where M can be an alkali metal ion, half an equivalent of an alkaline earth metal ion, an ammonium ion or an organic ammonium ion.

18. Process according to at claim 14, characterized in that X is chlorine, bromine, iodine, trifluoromethanesulphonyloxy or nonafluorobutanesulphonyloxy.

19. Process according to claim 14, characterized in that Y is fluorine, chlorine, bromine, iodine, methanesulphonyloxy, p-toluenesulphonyloxy, trifluoromethanesulphonyloxy or nonafluorobutanesulphonyloxy.

20. Process according to claim 14, characterized in that R$^1$ is hydrogen, cyano, $C_1$-$C_{12}$-alkyl, $C_5$-$C_{14}$-aryl, fluorine, chlorine, COO($C_5$-$C_{14}$-aryl), COO($C_1$-$C_2$-alkyl), OCO($C_5$-$C_{14}$-aryl) or OCO($C_1$-$C_{12}$-alkyl).

21. Process according to claim 14, characterized in that compounds of the formula (II) used are vinyl fluoride, vinyl chloride, vinyl bromide, 2-chloroacrylonitrile, methyl 2-chloroacrylate, butyl 2-chloroacrylate, 1,1-dichloroethylene, 1,1-dlfluoroethylene or 4-(1-chloroethenyl)-1,5-dimethyl-3-(trifluoromethyl)-1H-pyrazole.

22. Process according to claim 14, characterized in that palladium complexes generated in the reaction solution from suitable ligands or palladium complexes which have previously been isolated are used as palladium catalyst.

23. Process according to claim 14, characterized in that bases used are ionic bases, anilnes or N-heteroaromatic compounds.

24. Process according to claim 14, characterized in that free-radical inhibitors are added in step A).

25. Process according to claim 14, characterized in that bases used are alkaline earth metal or alkali metal hydrides, hydroxides, amides, alkoxides, tertiary amines and/or N-heteroaromatic compounds.

26. Process according to claim 14, characterized in that 4-ethynyl-1,5-dimethyl-3-(trifluoromethyl)-1H pyrazole is prepared.

* * * * *